United States Patent [19]

Schen

[11] Patent Number: 5,162,575
[45] Date of Patent: Nov. 10, 1992

[54] PREPARATION OF ISOCYANATES USING A SILVER SALT PROMOTED REARRANGEMENT

[75] Inventor: Ming Shen, Guilford, Conn.

[73] Assignee: Olin Corporation, Cheshire, Conn.

[21] Appl. No.: 678,394

[22] Filed: Apr. 1, 1991

[51] Int. Cl.$^5$ ............................................ C07C 263/12
[52] U.S. Cl. .................................... 560/338; 560/157; 560/162; 560/163; 560/330; 560/355; 560/358
[58] Field of Search ................................ 560/338, 330

[56] References Cited

U.S. PATENT DOCUMENTS

| | | | |
|---|---|---|---|
| 2,640,846 | 6/1953 | Hurwitz et al. | 560/338 |
| 4,238,404 | 12/1980 | Zeagel et al. | 560/338 |
| 4,282,167 | 8/1981 | Sy et al. | 560/338 |
| 4,683,329 | 7/1987 | Rao | 560/338 |

*Primary Examiner*—Jose G. Dees
*Assistant Examiner*—Vera C. Clarke
*Attorney, Agent, or Firm*—Dale Lynn Carlson

[57] ABSTRACT

The present invention relates to a process for producing isocyanates which comprises reacting an N-halogenated amide with an organic base in an essentially water-free modified Hofmann reaction using a soluble silver salt promoter in the presence of an organic solvent. Also disclosed is a process for producing a carbamate which comprises reacting an N-halogenated amide with an organic base in an essentially water-free modified Hofmann reaction using a soluble silver salt promoter in the presence of an alcohol solvent.

8 Claims, No Drawings

PREPARATION OF ISOCYANATES USING A SILVER SALT PROMOTED REARRANGEMENT

BACKGROUND OF THE INVENTION

Polyisocyanates are well-known precursors used in the manufacture of polyurethanes. In the past, commercial processes for the production of isocyanates have relied heavily on a phosgene-based production process. Unfortunately, phosgene is a toxic material that must be handled with caution. Accordingly, the industry has sought non-phosgene routes for the production of isocyanates.

Various methods for producing isocyanates by subjecting amides to modified Hofmann reactions are known in the art. The Hofmann reaction is "modified" in the sense that the reaction product is an organic isocyanate rather than an amine. As an illustrative example of such a reaction, U.S. Pat. No. 4,282,167 discloses using a 2-phase aqueous/organic system. Unfortunately this system is not as adaptable as might be desired, particulary since two-phase systems typically require the presence of water, and many isocyanates are water sensitive and must be produced in the absence of water. In addition, the disclosures of the '167 patent indicate that good product yields were only obtained for isocyanates with the isocyanate groups bonded to a secondary or a tertiary carbon. For others with the isocyanate groups bonded to a primary carbon, the yields were low, generally between 0% and 20%.

The production of isocyanates using a modified Hofmann reaction under anhydrous conditions is also known in the art. By way of illustration, U.S. Pat. No. 4,238,404 discloses a process for preparing isocyanates from the Hofmann rearrangement under anhydrous conditions using tertiary amine bases, but the disclosures of this patent are limited to isocyanates wherein the isocyanate groups are bonded to secondary or tertiary carbons. No disclosure of the production of any isocyanates with the isocyanate groups bonded to primary carbons is made in the '404 patent.

New non-phosgene methods for producing isocyanates in high yield from amines, especially methods that are essentially water-free and capable of producing primary isocyanates, would be highly desired by the urethanes manufacturing community.

SUMMARY OF THE INVENTION

In one aspect, the present invention relates to a process for producing isocyanates which comprises reacting an N-halogenated amide with an organic base in an essentially water-free modified Hofmann reaction using a soluble silver salt promoter in the presence of an organic solvent.

In another aspect, the present invention relates to a continuous process for producing an isocyanate which comprises the steps of:

(a) reacting an N-halogenated amide with an organic base in an essentially water-free modified Hofmann reaction employing a silver nitrate promoter in the presence of an organic solvent to produce an isocyanate and a silver halide salt, (b) reacting said silver halide with concentrated nitric acid in order to regenerate silver nitrate, and (c) repeating step (a) at least once using the silver nitrate produced in step (b) as a source of at least a portion of the silver nitrate employed in step (a).

In yet aspect, the present invention relates to the process for producing a carbamate which comprises reacting an N-halogenated amide with an organic base in an essentially water-free modified Hofmann reaction using a soluble silver salt promoter in the presence of an alcohol solvent.

These and other aspects will become apparent upon reading the following detailed description of the invention.

DETAILED DESCRIPTION OF THE INVENTION

It has been surprisingly found in accordance with the present invention that isocyanates are suitably produced in high yield by reacting an N-halogenated amide with an organic base in a modified Hofmann reaction in the presence of a soluble silver salt promoter and an organic solvent. The reaction is suitably employed to produce primary, secondary or tertiary isocyanates, as desired based upon the N-halogenated amide reactant selected, and can also be used to produce a carbamate if an alcohol solvent is employed. The present invention provides the only modified Hofmann reaction that produces primary isocyanates to the knowledge of the present inventor.

Preferred soluble silver salts for use in the present invention include the following: silver nitrate, silver nitrite, silver perchlorate, silver percholorite, and combinations thereof. The most preferred silver salt is silver nitrate. The silver salt is employed in an amount of at least about one molar equivalent based the amount of N-halogenated amide used, and preferably does not exceed a ten molar equivalent amount. After use in accordance with the process of the present invention, the silver is typically essentially fully recovered as the halide salt. The silver halide salt is then suitably treated with concentrated nitric acid in order to regenerate the desired silver nitrate (or other such salt) for re-use in the process of the present invention.

Suitable N-halogenated amides include the following aliphatic, cycloaliphatic, aromatic, and combinations thereof. Illustrative examples of suitable N-halogenated amides are the following: N-chlorononamide, N-bromo-n-butylamide, N-chloroisopropylamide, N-iodopentylamide, and the like.

Suitable organic bases include tertiary amines, such as, for example, triethyl amine, trimethyl amine, tripropyl amine, tri-n-butyl amine, ethyldimethyl amine, propyldimethyl amine, isopropyldimethyl amine, methyldiethyl amine, butyldimethyl amine, and combinations thereof, and the like. Also useful are pyridines such as, for example, 2,3,4,5-tetramethyl pyridine, 2,3,4,5,6-pentamethyl pyridine, N,N,N',N'-tertamethylethylene-diamine, and combinations thereof, and the like.

Suitable organic solvents are those that at least partially dissolve the silver salt employed in the process of the present invention. Preferably, the organic solvent is selected from the group consisting of acetonitrile, tetrahydrofuran, acetone, dimethyl sulfoxide, tetramethylene sulfoxide, dimethylforamide, dimethylacetamide, 1-methyl-2-pyrrolidinone, and combinations thereof. Most preferably, the organic solvent is acetonitrile, tetrahydrofuran, acetone, or a combination thereof. Other useful organic solvents include alcohols, thiols, and the like. Alcohols are suitably employed when the desired product is a carbamate, rather than an isocyanate. As an illustration, although it was found that a highly reactive isocyanate, phenyl isocyanate, was difficult to isolate in accordance with process of the present invention, methanol was suitably employed to provide the corresponding carbamate. The amount of solvent employed is suitably an amount sufficient to dissolve at least a portion of the silver salt promoter utilized in the process of the present invention.

The results achieved in accordance with the present invention are particularly surprising in view of the finding by the present inventor that N-halogenated amides reacted extremely slowly with organic bases (such as triethyl amine) at ambient temperature in the absence of a silver salt, and hardly any isocyanate is detected by infrared analysis after stirring this reaction mixture without the silver salt for a full day at ambient temperature. When more forceful conditions, such as refluxing in tetrahydrofuran, are employed, a complicated by-product mixture results. Also, no reaction is observed under moderate temperature and pressure conditions (i.e., room temperature and atmospheric pressure) when the N-halogenated amide is employed with a silver salt solution of an organic solvent but without the organic base.

The process of the present invention is suitably carried out at room temperature (e.g., 15°-30° C.) and atmospheric pressure, although higher or lower temperatures (e.g., −30° C.-100° C.) and pressures may be employed if desired. "Essentially water-free" means no more than 10%, preferably less than 1%, by weight of water is present in the reactants. A stoichiometric amount of each reactant is preferred for the reaction, but a molar equivalent range of between about 0.5 and about 10 for each other reactant can be suitably employed, based upon the amount of N-halogenated amide employed. The use of a molar excess of the organic base (e.g., triethyl amine) relative to the N-halogenated amide is preferred when using solvents such as tetrahydrofuran in order to increase the solubility of the silver salt. The order of addition of reactants is not critical, and all reactants can suitably be added simultaneously or step-wise, as desired.

The process of the present invention typically provides a high yield for isocyanates of greater than 70% by weight based upon the N-halogenated amide reactant in producing either isocyanates having isocyanato groups bonded to a primary carbon (so-called "primary isocyanates") or isocyanates having isocyanato groups bonded to a secondary carbon (so-called "secondary isocyanates"). In addition, the process of the present invention is suitable for use in the preparation of isocyanates with the isocyanato groups bonded to a tertiary carbon (so-called "tertiary isocyanates") and with multi-isocyanato groups, greater than 2, per molecule.

The isocyanates formed in situ from the Hofmann rearrangement could be trapped by a nucleophile such amines, The carbamate has the general formula R-(NHCO2R')n wherein R and R' represent an aliphatic, cycloaliphatic, aralphatic or aromatic group, and n represents an integral of at least 1. The process condition for the carbamates is similar to that for the isocyanates.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

EXAMPLE 1

Preparation of a Primary Isocyanate - n-Octyl Isocyanate 89 mg (0.52 mmol) of AgNO3 were added 3.5 ml of tetrahydrofuran and 150 ul (1.08 mmol) of triethyl amine, and stirred for 5 min. A grey colored solution thus obtained was added 100 mg (0.52 mmol) solids of N-chlorononamide in small portions. A white precipitate of AgCl was formed immediately. After stirring for 2 min. at ambient temperature, the reaction mixture was filtered and stripped. The remaining residue of triethyl ammonium nitrate and octyl isocyanate was added 5 ml of hexane to dissolve the isocyanate into solution. Filtration and stripping gave 52 mg (65% yield) of a clean liquid of octyl isocyanate with consistent FTIR and 1H NMR spectra.

EXAMPLE 2

Preparation of a Cyclic Isocyanate- Cyclohexyl Isocyanate 100 mg (0.59 mmol) of AgNO3 were dissolved in 4 ml of acetonitrile, and added 85 ul (0.61 mmol) of triethyl amine. 95 mg (0.59 mmol) of N-chlorocyclohexyl carboxamide were added in small portions. A white precipitate of AgCl was formed immediately. After stirring at ambient temperature for 2 min., the reaction mixture was filtered and stripped. The remaining residue was added 5 ml of hexane to dissolve the isocyanate into solution. Filtration and stripping gave 55 mg (46% yield) of cyclohexyl isocyanate with consistent FTIR and 1H NMR spectra.

EXAMPLE 3

Preparation of Aralkyl Isocyanate in THF-Phenylacetyl Isocyanate 50 mg (0.30 mmol) of AgNO3 were added 2 ml of tetrahyrofuran ("THF") and 85 ul (0.61 mmol) of triethyl amine, and stirred for 5 min. A grey colored solution thus obtained was added 50 mg (0.30 mmol) of N-chloro-2-phenylacetamide in small portions. After stirring at ambient temperature for 2 min., the AgCl precipitate was filtered and the filtrate was stripped. 26 mg (66% yield) of a clean liquid of benzyl isocyanate with consist FTIR and 1H NMR spectra were obtained.

EXAMPLE 4

Preparation of Primary Aliphatic Diisocyanate in Acetone 1,8-diisocyanatooctane 26 mg (0.15 mmol) of AgNO3 were partially dissolved in 8 ml of acetone, and added 20 mg (0.074 mmol) of N,N'-dichlorosebacamide which was completely dissolved in acetone. 21 ul (0.15 mmol) of triethyl amine were added dropwise from a 50 ul syringe. A white precipitate of AgCl was observed immediately. After stirring at ambient temperature for 40 min., the precipitate was filtered and the filtrate was stripped. The remaining residue was dissolved completely in 3 ml of methylene chloride and chromatographed quickly through a silica gel column. Stripping off solvent for the recovered isocyanate gave 11 mg (76% yield) of a clean liquid of 1,8-diisocyanatooctane with consistent FTIR and 1H NMR spectra.

EXAMPLE 5

Preparation of Primary Aliphatic Diisocyanate in Acetone 1,8-diisocyanatooctane 136 mg (0.8 mmol) of AgNO3 were partially dissolved in 42 ml of acetone, and added 100 mg (0.37 mmol) of N,N'-dichlorosebacamide which was completely dissolved in acetone. 105 ul (0.75 mmol) of triethyl amine were added dropwise from a syringe. After stirring at ambient temperature for 45 min., the AgCl precipitate was filtered and the filtrate was stripped. The remaining residue was added 3 ml of hexane to dissolve the isocyanate into solution. The insoluble triethylammonium nitrate was removed by filtration, and the filtrate was stripped. 49.4 mg (68% yield) of a clean liquid of 1,8-diisocyanato-octane was obtained.

EXAMPLE 6

Preparation of Primary Aliphatic Diisocyanate in THF 1,8-diisocyanatooctane 26 mg (0.15 mmol) of AgNO3 were partially dissolved in 3 ml of tetrahydrofuran ("THF"), and added 20 mg (0.074 mmol) of N,N'-di-chlorosebacamide which was completely dissolved in tetrahydrofuran. 21 ul (0.15 mmol) of triethyl amine were added dropwise. After reacting at ambient temperature for 3 hrs., the AgCl precipitate was filtered and the filtrate was concentrated. The addition of 2 ml of hexane to the concentrated residue gave a needle crystal of triethylammonium nitrate which is hygroscopic exposed to the air. Filtration and stripping gave 11.5 mg (79% yield) of a clean liquid of 1,8-diisocyanatooctane.

EXAMPLE 7

Preparation of Cyclic Diisocyanates- 1,4-diisocyanatocyclohexane in Triethyl Amine 285 mg (1.68 mmol) of AgNO3 were dissolved in 11 ml of acetonitrile, and added 235 ul (1.69 mmol) of triethyl amine. 200 mg (0.84 mmol) of N,N'-dichloro-1,4-cyclohexyl dicarboxamide were added in small portions. After stirring at ambient temperature for 20 min., the AgCl precipitate was filtered and the filtrate was stripped. The remaining residue was added 10 ml of ethyl ether. Stirring for additional 10 min., followed by filtration and stripping, 111 mg (75% yield) of a white solid of 1,4-diisocyanatocyclohexane were obtained. FTIR and 1HNMR spectra are consistent with those of an authentic sample.

EXAMPLE 8

Preparation of Methyl N-phdnyl Carbamate in Methanol 164 mg (0.97 mmol) of AgNO3 were dissolved in 5 ml of methanol, and added 150 mg of N-chlorobenzamide (0.96 mmol). 200 ul (1,43 mmol) of triethyl amine were added, subsequently, to bring out the white precipitate of AgCl. After stirring at ambient temperature for 2 hrs., the reaction mixture was filtered and stripped. The remaining residue was dissolved in 5 ml of methylene chloride, and washed three times with 1 ml of 0.1% HCl and three times with 1 ml of brine. The washed methylene chloride solution was dried over anhydrous MgSO4, filtered and stripped of solvent. 125 mg (86% yield) of a liquid, which solidified on standing, of the methyl ester of phenyl isocyanic acid were obtained. FTIR and 1H NMR spectra are consistent with those of an authentic sample prepared from phenyl isocyanate and methanol.

EXAMPLE 9

Preparation of an Aliphatic Dicarbamate-Dimethyl Ester of 1,8-Octane Diisocyanic Acid 130 mg (0.76 mmol) of AgNO3 were dissolved in 5 ml of methanol, and added 100 mg (0.38 mg) of N.N'-dichlorosebacamide. The clear solution thus obtained was added 150 ul (1.1 mmol) of triethyl amine. After stirring at ambient temperature for 2 hrs., the precipitate of AgCl was filtered and the filtrate was stripped. The remaining residue was dissolved in 5 ml of methylene chloride, and washed three times with 0.1% of HCl and three times with 1 ml of brine. The washed methylene chloride solution was dried over anhydrous MgSO4, filtered and stripped of solvent. 87.5 mg (89% yield) of a white solid of the dimethyl ester of 1,8-octanediisocyanic acid with consistent FTIR and 1H NMR spectra were obtained.

EXAMPLE 10

Preparation of Cyclic Carbamate - Methyl Ester of Cyclohexyl Isocyanic Acid 106 mg (0.62 mmol) of AgNO3 were dissolved in 5 ml of methanol, and added 90 ul (0.65 mmol) of triethyl amine. The grey colored solution thus obtained was added 100 mg (0.62 mmol) solids of N-chlorocyclohexyl carboxamide in small portions. After stirring at ambient temperature for 1.5 hrs., the AgCl precipitate was filtered and the filtrate was stripped. The remaining residue was dissolved in 5 ml of methylene chloride, and washed three times with 1 ml of 0.1% HCl and three times with 1 ml of brine. The washed methylene chloride solution was then dried over anhydrous MgSO4, filtered, and stripped of solvent. 79 mg (81.2% yield) of a white solid of the methyl ester of cyclohexyl isocyanic acid with consistent FTIR and 1H NMR were obtained.

What is claimed is:

1. A process for producing an isocyanate which comprises reacting an N-halogenated amide with an organic base in an essentially water-free reaction at a reaction temperature of between −30° C. and 100° C. using a soluble silver salt promoter, and employing an amount of said organic base and an amount of said silver salt of between about 0.5 and about 10 molar equivalents per molar equivalent of said N-halogenated amide employed, in the presence of an organic solvent selected from the group consisting of acetonitrile, tetrahydrofuran, acetone, dimethyl sulfoxide, tetramethylene sulfoxide, dimethylforamide, dimethylacetamide, 1-methyl-2-pyrrolidinone, and combinations thereof.

2. The process of claim 1 wherein said N-halogenated amide is selected from the group consisting of: aliphatic, cycloaliphatic, and aromatic N-halogenated amides.

3. The process of claim 1 wherein said N-halogenated amide is N-chlorononamide.

4. The process of claim 1 wherein said organic base is selected from the group consisting of triethyl amine, trimethyl amine, tripropyl amine, tri-n-butyl amine, ethyldimethyl amine, propyldimethyl amine, isopropyldimethyl amine, methyldiethyl amine, butyldimethyl amine, 2,3,4,5-tetramethyl pyridine, 2,3,4,5,6-pentamethyl pyridine, N,N,N',N'-tertamethylethylene-diamine, and combinations thereof.

5. The process of claim 1 wherein said silver salt is selected from the group consisting of: silver nitrate, silver nitrite, silver perchlorate, silver percholorite, and combinations thereof.

6. A continuous process for producing an isocyanate which comprises the steps of:
(a) reacting an N-halogenated amide with an organic base in an essentially water-free reaction at a reaction temperature of between −30° C. and 100° C. employing a soluble silver salt promoter, and employing an amount of said organic base and an amount of said silver salt of between about 0.5 and about 10 molar equivalents per molar equivalent of said N-halogenated amide employed, in the presence of an organic solvent selected from the group consisting of acetonitrile, tetrahydrofuran, acetone, dimethyl sulfoxide, tetramethylene sulfoxide, dimethylforamide, dimethylacetamide, 1-methyl-2-pyrrolidinone, and combinations thereof to produce an isocyanate and a silver halide salt,
(b) reacting said silver halide with concentrated nitric acid in order to regenerate silver nitrate, and
(c) repeating step (a) at least once using the silver nitrate produced in step (b) as a source of at least a portion of the silver nitrate employed in step (a).

7. The process of claim 6 wherein said N-halogenated amide is selected from the group consisting of: aliphatic, cycloaliphatic, and aromatic N-halogenated amides.

8. The process of claim 6 wherein said N-halogenated amide is N-chlorononamide.

* * * * *